(12) United States Patent
Jung et al.

(10) Patent No.: US 9,168,282 B2
(45) Date of Patent: Oct. 27, 2015

(54) METHOD FOR TREATING NEURONAL DAMAGE AND NEUROLOGICAL DISEASES

(71) Applicant: DONGKOOK PHARMACEUTICAL CO., LTD., Seoul (KR)

(72) Inventors: Jae-Hoon Jung, Busan (KR); Hyung-Ryong Moon, Busan (KR)

(73) Assignee: DONGKOOK PHARMACEUTICAL CO., LTD., Seoul (KR)

( * ) Notice: Subject to any disclaimer, the term of this patent is extended or adjusted under 35 U.S.C. 154(b) by 0 days.

(21) Appl. No.: 14/035,967

(22) Filed: Sep. 25, 2013

(65) Prior Publication Data

US 2014/0030366 A1 Jan. 30, 2014

Related U.S. Application Data

(63) Continuation of application No. 13/319,304, filed as application No. PCT/KR2010/002879 on May 6, 2010, now abandoned.

(30) Foreign Application Priority Data

May 7, 2009 (KR) ........................ 10-2009-0039860
May 6, 2010 (KR) ........................ 10-2010-0042276

(51) Int. Cl.
| | | |
|---|---|---|
| A61K 31/685 | (2006.01) | |
| A61K 36/886 | (2006.01) | |
| A61K 9/00 | (2006.01) | |
| A61K 9/107 | (2006.01) | |
| A61K 31/661 | (2006.01) | |
| A61K 31/688 | (2006.01) | |

(52) U.S. Cl.
CPC ............. *A61K 36/886* (2013.01); *A61K 9/0014* (2013.01); *A61K 9/107* (2013.01); *A61K 31/661* (2013.01); *A61K 31/685* (2013.01); *A61K 31/688* (2013.01)

(58) Field of Classification Search
None
See application file for complete search history.

(56) References Cited

U.S. PATENT DOCUMENTS

| | | | |
|---|---|---|---|
| 4,585,656 A | 4/1986 | Rosenthal et al. | |
| 5,744,461 A | 4/1998 | Hostetler et al. | |
| 6,004,579 A | 12/1999 | Bathurst et al. | |
| 6,080,744 A | 6/2000 | Ayon-Covarrubias et al. | |
| 6,143,278 A * | 11/2000 | Elkhoury | 424/45 |
| 6,197,830 B1 * | 3/2001 | Frome | 514/654 |
| 6,261,574 B1 | 7/2001 | Costello et al. | |
| 2004/0176323 A1 | 9/2004 | Song et al. | |
| 2004/0235949 A1 | 11/2004 | Kozak et al. | |
| 2005/0154190 A1 | 7/2005 | Mori et al. | |
| 2007/0243211 A1 | 10/2007 | Jaffe | |
| 2008/0051372 A1 | 2/2008 | Chun | |

FOREIGN PATENT DOCUMENTS

| | | |
|---|---|---|
| EP | 1 455 186 A1 | 9/2004 |
| JP | 1-135720 A | 5/1989 |
| JP | 2-215351 A | 8/1990 |
| JP | 6-116149 A | 4/1994 |
| JP | 6-157338 A | 6/1994 |
| JP | 2004-026803 A | 1/2004 |
| JP | 2005-272381 | 10/2005 |
| JP | 2007-119361 A | 5/2007 |
| WO | WO 95/20967 A1 | 8/1995 |
| WO | WO 97/09989 A1 | 3/1997 |
| WO | WO 01/12838 A2 | 2/2001 |
| WO | WO 02/092104 A1 | 11/2002 |

OTHER PUBLICATIONS

Homesteading Today, Internet forum, http://www.homesteadingtoday.com/general-homesteading-forums/homesteading-questions/36596-shingles.htm, Dec. 14, 2003.*
Overmeire et al, Effect of Aromatic Short-Chain Analogues of Ceramide on Axonal Growth in Hippocampal Neurons, Journal of Medicinal Chemistry, vol. 42, No. 14, Jan. 1, 1999, pp. 2697-2705.
Mervis R F et al, 50. Dietary-induced plasticity in the aging mouse brain: choline and phospatidylcholine promote new dendritic growth in old neurons, Clinical Neurology and Neurosurgery, Elsevier, Amsterdam, NL, vol. 89, No. 2, May 1, 1987, p. 18.
Shi F et al, Curataive effect of soybean lecithin on cerebral infarction, Zhonghua Yi Xue Za Zhi Nov. 2001, vol. 81, No. 21, Nov. 10, 2001, pp. 1301-1303.
Ma Lin et al, Lysophospatidic acid-3 receptor-mediated feed-forward production of lysophospatidic acid: an initiator of nerve injury-induced neuropathic pain, Molecular Pain, Biomed Central, London, GB, vol. 5, No. 1, Nov. 13, 2009, p. 64.
Daniela Kullenberg et al, Health effects of dietary phospholipids, Lipids in Health and Disease, Biomed Central, London, GB, vol. 11, No. 1, Jan. 5, 2012, p. 3.
European Search Report for European Patent Application No. 10772267.0 mailed Mar. 4, 2013 from European Patent Office.
David G. Kline, M.D., Civilian gunshot wounds to the brachial plexus, J. Neurosurg, Feb., 1989, pp. 166-174, vol. 70.
David G. Kline, M.D. et al., Operative management of selected brachial pluxus lesions, J. Neurosurg, May 1983, pp. 631-649, vol. 58.
Yeung Ki Kim, M.D. et al., Effects of Electrical Stimulation on Nerve Regeneration in . . . , J. of Korean Acad. of Rehab. Med., Oct. 1999, pp. 893-898, vol. 23, No. 5.

(Continued)

*Primary Examiner* — Layla Bland
(74) *Attorney, Agent, or Firm* — Revolution IP, PLLC

(57) ABSTRACT

Disclosed is a method of treating pain. The method includes administering a lecithin as an active ingredient to a mammal to treat the pain, wherein the pain is caused by at least one of herpes zoster, post-herpetic neuralgia, and diabetic neuropathic pain. The method further includes administering at least one selected from the group consisting of vegetable gel, a vegetable resin, and a synthetic resin, wherein the vegetable gel, vegetable resin, and synthetic resin is selected from the group consisting of aloe gel; a seaweed extract selected from the group consisting of kelp extract, agar extract, and Fucoidan; and a mixture thereof.

5 Claims, 10 Drawing Sheets

(56) References Cited

OTHER PUBLICATIONS

W. S. Al-Amood et al., Effects of Chronic Electrical Stimulation on Contractile Properties of Long-term Denervated Rat . . . , Journal of Physiology, 1991, pp. 243-256, vol. 441.

Millesi H., M.D., Brachial Plexus Injuries: Nerve Grafting, Clinical orthopaedics and related research, 1988, pp. 36-42, vol. 237.

Sung Bom Pyun, M.D. et al., Effect of Exercise on Reinnervating Solues Muscle after . . . , J. of Korean Acad. of Rehab. Med., Dec. 1999, pp. 1063-1075, vol. 23, No. 6.

Wim Opstel Ten MD PHD et a l., Treatment of herpes zoster, Can Fam Physician, Mar. 2008, pp. 373-377, vol. 54.

Stephen Typing, MD, PHD et al., Famciclovir for the Treatment of Acute Herpes Zoster . . . , Annals of Internal Medicinc, Jul. 15, 1995, pp. 89-96, vol. 123, No. 2.

\* cited by examiner

METHOD FOR TREATING NEURONAL DAMAGE AND NEUROLOGICAL DISEASES

CROSS REFERENCE TO PRIOR APPLICATIONS

This application is a Continuation application of U.S. patent application Ser. No. 13/319,304 filed on Nov. 7, 2011 under 35 U.S.C. §120, which is a National Stage Patent Application of PCT International Patent Application No. PCT/KR2010/002879 filed on May 6, 2010 under 35 U.S.C. §371, which claims priority to Korean Patent Application Nos. 10-2009-0039860 filed on May 7, 2009 and 10-2010-0042276 filed on May 6, 2010, which are all hereby incorporated by reference in their entirety.

BACKGROUND

The present invention relates to a pharmaceutical composition that effectively treats neuronal damage, such as damage of peripheral nerves or damage of central nerves, and neurological diseases, such as neuropathy, neuropathic pain or cerebropathy, by repairing damaged nerve tissues.

Various neurological diseases, such as Parkinson's disease, Alzheimer's disease, Huntington's disease, spino cerebellar degeneration, amyotrophic lateral sclerosis, polyneuropathy, spinal cord damage, cerebrovascular disorder, or the like, develop due to degeneration, reduction, cell death, or damage or exclusion of brain or peripheral neurons caused by, for example, environmental or hereditary factors. Accordingly, in treating these neurological diseases, it is important to either compensate for a neuron delivery material that is removed by damage of neurons or regenerate neurons. To regenerate neurons, an undifferentiated neuron stem cell, an embryonic stem cell that can be differentiated into various other cells, etc. may be used.

A great deal of research has been performed on neuron regeneration of damaged neuron. In general, a clinical physical treatment method on traumatic damage of peripheral neurons includes complicated and sequential steps: first, a damaged tissue near a damaged tropical region is removed and then, environments that enable regeneration of peripheral neurons (Kline, J Neurosurg, 1989, 70: 166-174) are provided. Typically, the physical process includes a direct connection or fusion between a portion that is located closer to the damaged region and a farther portion (Kline and Judice, J Neurosurg, 1983, 58: 631-649). During waiting for spontaneous regeneration of neurons, an additional physical method, such as peripheral neuron transplantation (Millesi, Clin Orthop Relat R, 1988, 237: 36-42), is used, as well as a more prudent outpatients treatment, such as maintaining of electrical excitation to generate contraction of muscle to help suppression of deterioration of a muscle-neuron unity (Kim et al., Korean Academy of Rehabilitation Medicine (Korean), 1999, 23: 893-898; al-Amood et al., J Physiol (Lond), 1991, 441: 243-256). Also, these processes still include a comprehensive physical treatment method including a long-term and controlled exercise therapy to prevent weakness and contraction of muscle and to promote neuron blast (Pyun et al., Korean Academy of Rehabilitation Medicine (Korean), 1999, 23: 1063-1075).

Recently, a report was disclosed that neurogenesis in the hippocampus of an adult brain has been reported, and the report has led to development of a method of treating neurological disease by stimulating neuron stem cells in a patient's brain with, for example, a drug to induce regeneration thereof. However, the method requires injection of protein or a protein factor into the brain and is not applicable to general practices. Accordingly, as an alternative to the protein, a low molecular weight compound salvianolic acid B or lithium or a pharmaceutically available salt thereof has been introduced.

Also, damage of peripheral neuron induces a change in a cell body of sensory neuron located at dorsal root ganglion (DRG) for promoting survival and regeneration of axon. For example, after crushing injury, under improved disorder conditions, most neuron fibers are successfully regenerated. However, in many clinical situations, traumatic or disease-induced neuron damage results in limited repair and, in general, substantial delay. In this case, neuropathic or chronic pain may develop.

A representative example of neuropathic pain includes herpes zoster and post-herpetic neuralgia, and these neuropathic pains are, in many cases, comparable to a labor pain which is known as the strongest pain in the life, in terms of a pain level. Also, unlike other diseases causing strong pain, such as terminal cancerous pain, gouty seizure, and trigeminal neuralgia, they are continuous pain, not periodical pain.

Regarding herpes zoster, currently available antivirus agents, for example, acyclovir, valaciclovir, famciclovir, and penciclovir, as described in their prescription guide lines, are therapeutically effective to a certain level only when used within 72 hours after initial rash of herpes zoster. However, many patients visit hospitals after the 72 hours. Accordingly, their effectiveness is reduced in half.

Furthermore, regarding herpes zoster and post-herpetic neuralgia, allopathic agents for reducing neuralgia are used. Examples of the allopathic agents are a non steroidal anti-inflammatory analgesic drug, such as acetaminophen or piroxicam; a narcotic analgesic, such as morphine, oxycodone, pentanyl, or codein; an antiepileptic, such as gabapentin, pregabalin, or valproate; an antidepressant, such as nortriptyline, desipramine, or amitriptyline; an adrenal cortex hormone, such as prednisolone; and a topical anesthetic, such as lidocaine. However, typically, the allopathic agents are not effective and if pain is strong or lasts long, neuron blocking techniques are actively used.

Currently, a prescription for the herpes zoster treatment mainly includes use of an antivirus agent and an anti-inflammatory analgesic drug, and is not effective for repairing damaged nerve tissue, which is an etiological factor of herpes zoster and post-herpetic neuralgia. Thus, it is impossible to effectively control pain.

Also, there is an increasing demand for developing a therapeutic agent for directly preventing or treating a disease that induces damage of nerve tissue, like herpes zoster and post-herpetic neuralgia. Examples of such a disease are neuropathy or neuropathic pain, such as acute inflammatory demyelinating peripheral polyneuropathy, chronic inflammatory demyelinating peripheral polyneuropathy, diabetic peripheral neuropathy, vasculitis neuropathy, hereditary peripheral neuropathy, stroke, brain tumor, degenerative neurological disease, painful diabetic peripheral neuropathy, trigeminal neuralgia, carcinomatous neuro-pathy occurring along cerebral cortex or spinothalamic tract, post-traumatic neuropathy, phantom limb pain, post-stroke central pain, or thalamic pain, and cerebropathy, such as stroke, brain tumor, dementia, Parkinson's disease, Alzheimer's disease, Huntington's disease, epilepsy, dementia, or ischemic cerebropathy.

Accordingly, a drug for effectively treating neuronal damage or neurological disease by rapidly repairing damage of nerve tissue needs to be developed.

SUMMARY

The present invention provides a pharmaceutical composition for preventing or treating neuronal damage and neurological diseases, based on the fact that a compound represented by Formula 1 or Formula 2 repairs damaged nerves to effectively prevent or treat neuronal damage, such as damage of peripheral nerves or damage of central nerves, and neurological diseases, such as neuropathy, neuropathic pain or cerebropathy.

According to an aspect of the present invention, there is provided a pharmaceutical composition for preventing or treating neuronal damage and neurological disease, wherein the pharmaceutical composition includes as an active ingredient at least one compound selected from the group consisting of a compound represented by Formula 1 below, a compound represented by Formula 2 below, and an available salt thereof:

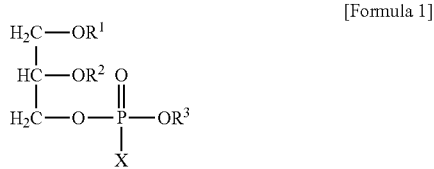

[Formula 1]

in Formula 1, X is OH, SH or $O^-$, $R^1$, $R^2$, and $R^3$ are each a linear or cyclic alkyl, alkenyl or alkynyl, $-C(=O)R^4$, $-(CH_2)nOH$, $-(CH_2)nNR^5R^6$, $-(CH_2)nN^+R^7R^8R^9$, $-CH_2CH(COOH)NH_2$, $-CH_2CH(COO^-)NH_2$, $-CH_2CH(COOH)NH_3^+$, inositol, pentose, hexose, glycerol, phosphatidyl glycerol, or H, n is an integer of 1 to 10, and $R^4$, $R^5$, $R^6$, $R^7$, $R^8$, and $R^9$ are each a linear or cyclic alkyl, alkenyl or alkynyl, or H, and

[Formula 2]

in Formula 2, $R^1$, $R^2$, $R^3$, $R^4$, and $R^5$ are each a linear or cyclic alkyl, alkenyl or alkynyl, $-C(=O)R^6$, phosphocholine, phosphoric acid, pentose, hexose or a derivative of these saccharides, an amino sugar, an alkoxy phosphoric acid, or H, and $R^6$ is a linear or cyclic alkyl, alkenyl, or alkynyl.

The neuronal damage and neurological disease may be any disorder selected from the group consisting of damage of peripheral nerves, damage of central nerves, neuropathy, neuropathic pain, and cerebropathy.

Also, the pharmaceutical composition may further include at least one selected from the group consisting of a vegetable gel, a vegetable resin, and a synthetic resin.

Also, the pharmaceutical composition may include 0.1 to 99.9 wt % of the at least one compound selected from the group consisting of the compound represented by Formula 1, the compound represented by Formula 2, and an available salt thereof and 0.1 to 99.9 wt % of the at least one selected from the group consisting of a vegetable gel, a vegetable resin, and a synthetic resin.

The at least one compound selected from the group consisting of the compound represented by Formula 1, the compound represented by Formula 2, and an available salt thereof used as an active ingredient repairs damaged nerve tissues quickly to effectively prevent or treat neuronal damage and neurological diseases, such as neuropathy, neuropathic pain or cerebropathy.

DETAILED DESCRIPTION

Figure 1:
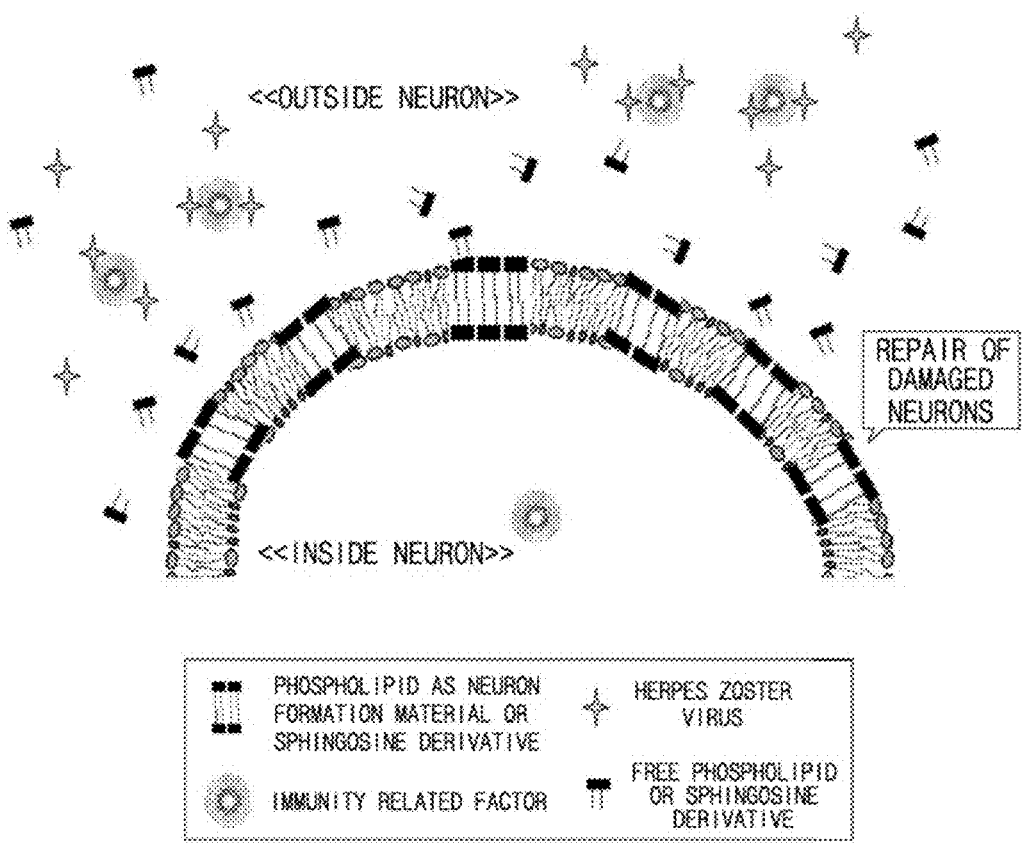
FIG. 1 is a schematic view for explaining how a nerve region that is damaged by budding of a herpes zoster virus is repaired by filling with a phospholipid or sphingosine derivative contained in the pharmaceutical composition according to the present invention.

The present invention provides a pharmaceutical composition for preventing or treating neuronal damage and neurological disease, wherein the pharmaceutical composition includes as an active ingredient at least one compound selected from the group consisting of a compound represented by Formula 1 below, a compound represented by Formula 2 below, and an available salt thereof:

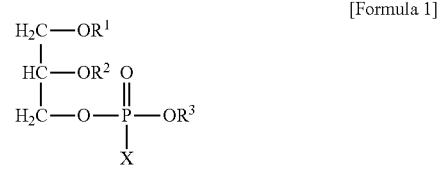

[Formula 1]

in Formula 1, X is OH, SH or $O^-$, $R^1$, $R^2$, and $R^3$ are each a linear or cyclic alkyl, alkenyl or alkynyl, $-C(=O)R^4$, $-(CH_2)nOH$, $-(CH_2)nNR^5R^6$, $-(CH_2)nN^+R^7R^8R^9$, $-CH_2CH(COOH)NH_2$, $-CH_2CH(COO^-)NH_2$, $-CH_2CH(COOH)NH_3^+$, inositol, pentose, hexose, glycerol, phosphatidyl glycerol, or H, n is an integer of 1 to 10, and $R^4$, $R^5$, $R^6$, $R^7$, $R^8$, and $R^9$ are each a linear or cyclic alkyl, alkenyl or alkynyl, or H, and

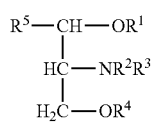 [Formula 2]

in Formula 2, $R^1$, $R^2$, $R^3$, $R^4$, and $R^5$ are each a linear or cyclic alkyl, alkenyl or alkynyl, —C(=O)$R^6$, phosphocholine, phosphoric acid, pentose, hexose or a derivative of these saccharides, an amino sugar, an alkoxy phosphoric acid, or H, and $R^6$ is a linear or cyclic alkyl, alkenyl, or alkynyl.

The compound may be selected from the group consisting of phosphatidylcholines, phosphatidylethanolamines, phosphatidylserines, phosphatidylinositols, phosphatidic acids, sphingophospholipids, sphingomyelins, plasmalogens, sphingoplasmalogens, phosphatidyl glycerol, cardiolipins, cerebrosides, ceramides, lyso-type materials thereof and available salts thereof.

The neuronal damage and neurological disease may be selected from the group consisting of damage of peripheral nerves, damage of central nerves, neuropathy, neuropathic pain, and cerebropathy.

The neuropathy or neuropathic pain may be selected from the group consisting of acute inflammatory demyelinating peripheral polyneuropathy, chronic inflammatory demyelinating peripheral polyneuropathy, diabetic peripheral neuropathy, herpes zoster, vasculitis neuropathy, hereditary peripheral neuropathy, spino cerebellar degeneration, amyotrophic lateral sclerosis, painful diabetic peripheral neuropathy, trigeminal neuralgia, carcinomatous neuro-pathy occurring along cerebral cortex or spinothalamic tract, post-traumatic neuropathy, post-herpetic neuralgia, phantom limb pain, post-stroke central pain, and thalamic pain.

Also, preferably, the neuropathy or neuropathic pain may be selected from the group consisting of diabetic peripheral neuropathy, herpes zoster, vasculitis neuropathy, painful diabetic peripheral neuropathy, trigeminal neuralgia, post-traumatic neuropathy, post-herpetic neuralgia, and phantom limb pain. More preferably, the neuropathy or neuropathic pain may be selected from the group consisting of diabetic peripheral neuropathy, herpes zoster, painful diabetic peripheral neuropathy, trigeminal neuralgia, and post-traumatic neuropathy, and post-herpetic neuralgia. The most preferably, the neuropathy or neuropathic pain may be selected from the group consisting of herpes zoster and post-herpetic neuralgia.

Also, the cerebropathy may be selected from the group consisting of stroke, brain tumor, dementia, Parkinson's disease, Alzheimer's disease, Huntington's disease, epilepsy, and ischemic cerebropathy.

Also, the damage of peripheral nerves or damage of central nerves may be selected from the group consisting of neurotmesis and traumatic neuronal damage.

Also, the pharmaceutical composition may further include at least one selected from the group consisting of a vegetable gel, a vegetable resin, and a synthetic resin.

The vegetable gel, vegetable resin, and synthetic resin may be selected from the group consisting of aloe gel; a seaweed extract selected from the group consisting of kelp extract, agar extract, and Fucoidan; a vegetable or synthetic resin that functions like the foregoing; and a mixture thereof.

The pharmaceutical composition may include 0.1 to 99.9 wt % of the at least one compound selected from the group consisting of the compound represented by Formula 1, the compound represented by Formula 2, and an available salt thereof and 0.1 to 99.9 wt % of the at least one selected from the group consisting of a vegetable gel, a vegetable resin, and a synthetic resin.

The pharmaceutical composition may further include a support, an aid, or a vehicle which are typically used in preparing the pharmaceutical composition. Examples of the available support, aid, and vehicle used herein are an ionexchanger, alumina, aluminum stearate, serum protein such as human serum albumin, a buffer material such as phosphate, glycine, sorbic acid, potassium sorbate, a partially glyceride mixture of saturated vegetable fatty acid, water, protamine sulfate, disodium hydrogen phosphate, potassium hydrogen phosphate, sodium chloride, salt, such as zinc salt, or electrolyte, colloidal silica, magnesium trisilicate, polyvinyl pyrrolidone, a cellulose-based material, polyethylene glycol, sodium carboxymethylcellulose, polyacrylate, wax, polyethylene-polyoxypropylene-block polymers, polyethylene glycol, and wool fat.

The pharmaceutical composition according to the present invention may be administered to a mammal, such as a rat, a mouse, livestock, or a human, through various paths. All of administration methods are expectable. For example, the administration may be performed orally, non-orally, by injection, by using a needle-free device, by inhalation spraying, topically, through a rectal or nose, buccally, vaginally, or through an implanted reservoir. Preferably, the administration method may be an oral administration, or an injection administration, a needle-free device-using administration, or dermal administration. The term "non-oral" used herein includes transdermal administration, and subcutaneous, intracutaneous, intravenous, intramuscular, intra-articular, intrasynovial, intrasternal, intrathecal, intralesional, and intracranial injection or infusion techniques.

When the pharmaceutical composition is administered by injection or by using a needle-free device, the pharmaceutical composition may be prepared in a formulation that is sterile injectable or a formulation that is appropriate for delivery using a needle-free device, and these formulations may be a water-soluble suspension or an oil-based suspension. These suspensions may be formulated by using an appropriate dispersing agent, wetting agent, or suspending agent according to a commonly known method in the art. Also, the sterile injectable formulation or the formulation that is appropriate for delivery using a needle-free device may be a solution or suspension in a non-toxic and non-orally acceptable dilute solution or solvent, for example, a solution in 1,3-butandiol.

As an available vehicle and solvent, mannitol, water, a Ringer's solution, and an isotonic sodium chloride solution may be used. Also, a sterile fixed oil may be typically used as a solvent or a suspension medium. For this purpose, a less stimulative fixed oil including synthetic mono-diglyceride may be used. A fatty acid, such as oleate and a glyceride derivative thereof, may be useful in preparing an pharmaceutically available oil, such as olive oil or castor oil, in particular, their polyoxyethylated versions, as an injectable formulation.

The pharmaceutical composition may be orally administered in an orally available formulation, such as capsules, tablets, or a water-soluble suspension and solution. However, the administration method and formulation are not limited thereto. Regarding tablets for oral administration, examples of a typically used support are lactose and corn starch. Also, typically, a lubricant, such as magnesium stearate, may be added thereto. A useful dilute solution for use in the capsule formulation for oral administration may include lactose and dry corn starch. When a water-soluble suspension is administered orally, an active ingredient may be combined with an emulsifier and a suspending agent. If desired, a sweetener and/or a flavoring agent and/or a coloring agent may be added thereto.

The pharmaceutical composition may be administered topically, and the topical administration may be particularly useful when a desired treatment is related to a region or tissue that is highly accessible by topical application. For topical application to a skin, the pharmaceutical composition needs to be formulated into an appropriate ointment containing an active ingredient suspended or dissolved in a support. Non-limiting examples of the support for the topical administration of the pharmaceutical composition according to the present invention are mineral oil, liquid petroleum, white petroleum, propylene glycol, a polyoxyethylene-polyoxypropylene compound, oily wax, and water.

Also, the pharmaceutical composition according to the present invention may be formulated into an appropriate lotion or cream containing an active ingredient suspended or dissolved in a support. Examples of the support are mineral oil, sorbitan monostearate, polysorbate 60, cetyl ester wax, cetearyl alcohol, 2-octyldodecanol, benzyl alcohol, and water. Also, the pharmaceutical composition according to the present invention may be prepared into a rectal suppository formulation or an enema formulation for topical application into a lower intestinal tract. The pharmaceutical composition according to the present invention may also be formulated into topical-transdermal patch.

The pharmaceutical composition according to the present invention may be administered by using a nose aerosol or by inhalation. The pharmaceutical composition may be formulated according to widely known techniques in the pharmaceutical formation field. For example, the pharmaceutical composition may be prepared as a solution in a saline solution by using benzyl alcohol or other appropriate preserving agent, an absorption promoter for increasing bioavailability, fluorocarbon, and/or other dissolving agents or dispersants known in the art.

It would be obvious to those of ordinary skill in the art that the selected levels or ranges of necessary or arbitrary components described herein may be dependent on formulation of a composition for direct use or a concentrate that is to be diluted before use, an ultimate use of selected particular component or the composition, and other factors that are known to those of ordinary skill in the art.

Regarding the pharmaceutical composition according to the present invention, a dosage of at least one compound selected from the group consisting of the compound represented by Formula 1, the compound represented by Formula 2, and an available salt thereof may be typically in a range of about 100 to about 10,000 mg/60 kg (body weight) once, and the dosage may be applied two or three times per day. The dosage may vary according to the age, gender, body weight, seriousness of disease, body conditions, etc. of a patient.

Also, when the pharmaceutical composition according to the present invention is topically applied, a dosage and an administration frequency may vary according to various factors of a patient who is to be treated, including the age, gender, body weight, seriousness of disease, size of a disease site, body conditions, etc. of the patient, and an active component concentration, etc. Typically, the pharmaceutical composition may be, for most use, applied in a dosage of 10 mg/cm$^2$ or more, preferably 50 mg/cm$^2$ or more, more preferably 100 mg/cm$^2$ or more, and the most preferably 200 mg/cm$^2$ or more, per 1 square centimeter. The applying may be performed once or several times (for example, 2 to 6 times) everyday for one or more days, and typically, the pharmaceutical composition may be applied once or two times per day for 1 to 14 days.

Examples will now be presented below to help understanding of the present invention. However, the examples are provided for illustrative purpose only and the present invention is not limited thereto.

EXAMPLE 1

Preparation of H-Z Cream 0.7 g of potassium hydroxide and 10 mL of glycerin were dissolved in 75 mL of purified water in a 200 mL beaker and then the solution was heated at a temperature of 80 to 85° C. This solution was added to a liquid stearic acid prepared by completely melting 15 g of stearic acid in a 250 mL beaker in a water bath at a temperature of 80 to 85° C. and stirred and cooled to room temperature, thereby preparing a vanishing cream.

100.7 g of the prepared vanishing cream was added to 229.0 g of aloe vera gel and the mixture was sufficiently mixed. Then, 16.03 g of Oronia Soybean Lecithin (supplier: Deraco Natural Source Company LTD.) as a phospholipid or sphingosine derivative, 1.60 g of alpha-tocopherol, and 0.50 g of propyl benzoate were each added thereto in small portions while stirring, thereby preparing a light yellowish cream. The resultant composition included 1.7 wt % of phospholipid or a sphingosine derivative.

EXAMPLE 2

Preparation of H-Z Cream 4.00 g of Tween #80 was added to 200.0 g of aloe vera gel and the mixture was sufficiently mixed. Then, 20.00 g of Oronia Soybean Lecithin (supplier: Deraco Natural Source Company LTD.), 2.00 g of alpha-tocopherol, and 0.30 g of propyl benzoate were each added thereto in small portions while stirring, thereby preparing a light yellowish cream. The resultant composition included 3.24 wt % of phospholipid or a sphingosine derivative.

EXAMPLE 3

Preparation of H-Z Cream 14.00 g of Tween #80 was added to 127.0 g of aloe vera gel and the mixture was sufficiently mixed. Then, 70.00 g of GL-90E (supplier: GoshenBiotech) as phospholipid or a sphingosine derivative, 7.00 g of alpha-tocopherol, and 0.30 g of propyl benzoate were each added thereto in small portions while stirring, thereby preparing a light yellowish cream. The resultant composition included 29.1 wt % phospholipid or a sphingosine derivative.

EXPERIMENTAL EXAMPLE 1

Clinical Test Analysis on Herpes Zoster and Post-herpetic Neuralgia

Clinical tests for herpes zoster and post-herpetic neuralgia were performed using the compositions (referred to as H-Z cream) prepared according to Examples 1 to 3 by using a method described below.

1. Test Hospital Name: O O Hospital
2. Test Physician: O O O, the head of O O department
3. Test Period: Oct. 28, 2008 to Mar. 15, 2009
4. Number of Patients with respective diseases
   1) Herpes zoster: 33 patients
   2) Post-herpetic neuralgia: 8 patients
5. Age distribution (Table 1)

TABLE 1

| Age | Patients (number) |
|---|---|
| Age of 30 to 39 | 3 |
| Age of 40 to 49 | 6 |
| Age of 50 to 59 | 14 |
| Age of 60 to 69 | 10 |
| Age of 70 to 79 | 4 |
| Age of 80 or more | 4 |

6. Herpes zoster Patient Analysis
   1) Hospital Visit Time
      ① within 72 hours after rash: 11 patients
      ② after 72 hours after rash: 22 patients (3 days after: 14 patients, 4 days after: 5 patients, and 7 days after: 3 patients)
   2) Treatment Method
      ① 500 mg (three times per day, for 7 days) of Famciclovir and H-Z cream application (once per day when visited hospital)
      ② H-Z cream application alone (once per day when visited hospital)—Kim Jong-sook (46), Lim Jeong-bu (67)
      ③ H-Z cream application method: H-Z cream was applied on a skin lesion region in a thickness of about 3.0 mm and then sealed with polyethylene wrap
   3) Progress of Skin Lesion Over Time (Steps 1 to 6)

Herpes zoster progress was evaluated in the following steps, and results thereof are classified as below. The results are shown in Table 2.

(1) Step 1: skin lesion does not occur but pain may occur.
(2) Step 2: small bumps are generated after rash
(3) Step 3: small bumps are agglomerated to form blisters
(4) Step 4: blisters are filled with a lymph fluid and burst
(5) Step 5: scab is generated and reduced
(6) Step 6: skin lesion almost disappears and processes into post-herpetic neuralgia

TABLE 2

| | | Skin lesion progress step according to treatment date | | | | | | | | | |
|---|---|---|---|---|---|---|---|---|---|---|---|
| | Applied Composition | Date 0[I] | Date 1 | Date 2 | Date 3 | Date 4 | Date 5 | Date 6 | Date 7 | Date 8 | Date 9 |
| Lee An-u (54) | Example 1 | 4[II] | 5 | | | | | | | | |
| Lee Sang-jun (60) | Example 1 | 3 | 4 | 5 | | | | | | | |
| Choi Hae-suk (58) | Example 1 | 2 | 3 | 3 | 4 | 5 | | | | | |
| An Ok-soon (41)[III,VII] | Example 1 | 2 | 2 | 1 | | | | | | | |
| Kim Hui-suk (51)[IV] | Example 1 | 3 | 2 | [VI]— | 1 | | | | | | |
| Kwon Gyeong-chun (83) | Example 2 | 3 | — | 4 | — | 5 | | | | | |
| Lee Soo-hyeon (56)[VII] | Example 2 | 2 | — | 2 | — | — | 5 | | | | |
| Bae Sook-hyeon (35) | Example 2 | 3 | 4 | — | — | 5 | | | | | |
| Han Sang-woo (81) | Example 2 | 4 | 5 | | | | | | | | |
| Nho Mu-ho (37) | Example 2 | 3 | 4 | — | 5 | | | | | | |
| Kim Jeom-yul (75) | Example 2 | 3 | — | 5 | | | | | | | |
| Jo Deok-pil (59)[V] | Example 2 | 3 | 2 | 2 | 1 | | | | | | |
| Kim Won-jo (90) | Example 2 | 4 | 5 | | | | | | | | |
| Shin Hui-nam (69) | Example 2 | 3 | — | 4 | 4 | — | 5 | | | | |
| Song Tae-sin (50) | Example 2 | 3 | — | 3 | 5 | | | | | | |
| Park Yeong-hwa (63) | Example 2 | 3 | 4 | 4 | 5 | | | | | | |
| Park Chun-taek (64) | Example 2 | 3 | 4 | 5 | | | | | | | |

TABLE 2-continued

| | Applied Composition | Date 0[I] | Date 1 | Date 2 | Date 3 | Date 4 | Date 5 | Date 6 | Date 7 | Date 8 | Date 9 |
|---|---|---|---|---|---|---|---|---|---|---|---|
| Lee Mal-nam (53) | Example 2 | 3 | — | — | 5 | | | | | | |
| Lee Du-ri (59) | Example 2 | 4 | 5 | | | | | | | | |
| Seon Jong-man (56)[VII] | Example 2 | 3 | 4 | — | 4 | 5 | | | | | |
| Kim Jong-sook (46) | Example 3 | 3 | 4 | — | 5 | | | | | | |
| Kim Dong-joon (60) | Example 3 | 3 | 4 | 5 | | | | | | | |
| Park Ui-yong (39) | Example 3 | 3 | — | 5 | | | | | | | |
| Kim Gyu-do (49)[VII] | Example 3 | 3 | 4 | 5 | | | | | | | |
| Choi Byeong-gi (68) | Example 3 | 3 | — | 5 | | | | | | | |
| Park Deok-man (73)[VII] | Example 3 | 3 | — | 5 | | | | | | | |
| Park Gwang-il (50)[VII] | Example 3 | 3 | — | 5 | | | | | | | |
| Lim Jeong-bu (67) | Example 3 | 4 | 5 | | | | | | | | |
| Seong Yeong-yun (40)[VII] | Example 3 | 3 | — | 5 | | | | | | | |
| Lee Soo-gi (78)[VII] | Example 3 | 3 | 3 | 3 | — | 4 | 4 | 5 | | | |
| Kim Deok-soon (51)[VII] | Example 3 | 3 | — | 5 | | | | | | | |
| Choi Gyo (85)[VII] | Example 3 | 3 | 3 | 3 | — | 3 | 5 | | | | |
| Hwang Bong-ok (71)[VII] | Example 3 | 3 | — | 3 | — | 4 | — | — | 5 | | |

Figure 2:
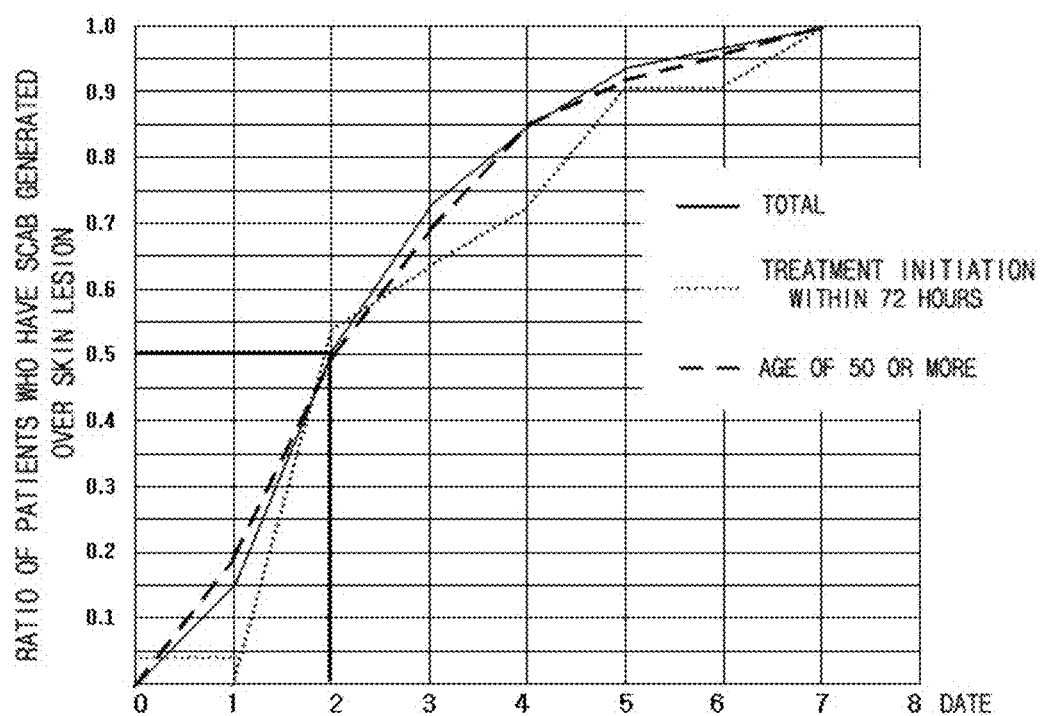
FIG. 2 shows a median of time required to generate a scab over a whole skin lesion.

[I]the first hospital visit date is represented by "Date 0", and the other dates after the first visit are represented by Date 1, Date 2 ...
[II]progress level of skin lesion of herpes zoster is classified as one to six steps.
[III,IV,V]small bumps do not progress into the scab generation step and blisters are abated and disappear
[VI]the date when patients do not visit the hospital is represented by '—'
[VII]treatment begins within 72 hours after rash Also, a median of time required for generating scab over the whole skin lesion is illustrated in FIG. 2.

4) Acute Pain Level Change Over Time[I] (in a Scale of 0 to 10)

Acute pain level change over time (in a scale of 0 to 10) is shown in Table 3 below.

TABLE 3

| | Date 0[II] | Date 1 | Date 2 | Date 3 | Date 4 | Date 5 | Date 6 | Date 7 | Date 8 | Date 9 |
|---|---|---|---|---|---|---|---|---|---|---|
| Lee An-u (54) | 4[III] | 3 | — | [IV]— | * | — | — | — | — | 0 |
| Lee Sang-jun (60) | 5 | 4 | 3 | 2 | — | — | — | — | — | — |
| Choi Hae-suk (58) | 5 | 8 | 5 | 4 | 3 | — | — | * | — | — |
| An Ok-soon (41)[V] | 3 | 2 | — | — | — | — | — | — | — | — |
| Kim Hui-suk (51) | 4 | 3 | — | 2 | — | — | — | — | — | — |
| Kwon Gyeong-chun (83) | 5 | — | 4 | — | 4 | — | 3 | — | — | * |
| Lee Soo-hyeon (56)[V] | 4 | — | 3 | — | — | 2 | — | — | — | — |

TABLE 3-continued

| | Acute pain level change according to treatment date (points 0 to 10)) | | | | | | | | | |
|---|---|---|---|---|---|---|---|---|---|---|
| | Date 0[II] | Date 1 | Date 2 | Date 3 | Date 4 | Date 5 | Date 6 | Date 7 | Date 8 | Date 9 |
| Bae Sook-hyeon (35) | 6 | 3 | — | — | 3 | — | — | * | — | — |
| Han Sang-woo (81) | 3 | 3 | — | 2 | — | 1 | — | — | — | — |
| Nho Mu-ho (37) | 5.5 | 4 | — | 2 | — | — | — | 1 | — | — |
| Kim Jeom-yul (75) | 6 | — | 3 | — | — | * | — | — | — | — |
| Jo Deok-pil (59) | 3 | 2 | 2 | 1 | — | — | — | — | — | — |
| Kim Won-jo (90) | 7 | 4 | — | 2 | — | — | — | — | — | — |
| Shin Hui-nam (69) | 5 | — | 4 | 4 | — | 1 | — | — | — | — |
| Song Tae-sin (50) | 5.5 | — | 5 | 3 | — | — | * | — | — | — |
| Park Yeong-hwa (63) | 7 | 6 | 5 | 3 | 2 | 1 | — | — | — | — |
| Park Chun-taek (64) | 5 | 5 | 3 | — | — | — | — | — | — | — |
| Lee Mal-nam (53) | 3 | — | — | 2 | — | — | — | — | — | — |
| Lee Du-ri (59) | 6 | 5 | 4 | 4 | 3 | 2 | — | — | — | — |
| Seon Jong-man (56)[V] | 7 | 6 | — | 5 | 4 | 3 | — | — | * | — |
| Kim Jong-sook (46) | 6 | 4 | — | 2 | — | — | — | — | — | — |
| Kim Dong-joon (60) | 6.5 | 4 | 3 | — | — | * | — | — | — | — |
| Park Ui-yong (39) | 7 | — | 3 | — | — | * | — | — | — | — |
| Kim Gyu-do (49)[V] | 5 | 4 | 1 | — | — | — | — | — | — | — |
| Choi Byeong-gi (68) | 3 | — | 1 | — | — | — | — | — | — | — |
| Park Deok-man (73)[V] | 5 | — | 2 | — | — | — | — | — | — | — |
| Park Gwang-il (50)[V] | 5 | — | 3 | — | — | * | — | — | — | — |
| Lim Jeong-bu (67) | 2 | 1 | — | — | — | — | — | — | — | — |
| Seong Yeong-yun (40)[V] | 3 | — | 1 | — | — | — | — | — | — | — |
| Lee Soo-gi (78)[V] | 5 | 5 | 4 | — | 3 | 2 | 1 | — | — | — |
| Kim Deok-soon (51)[V] | 1 | 1 | 1 | — | — | — | — | — | — | — |
| Choi Gyo (85)[V] | 5 | 4 | 3 | — | 2 | 1 | — | — | — | — |
| Hwang Bong-ok (71)[V] | 7 | — | 5 | — | 3 | — | — | 0 | — | — |

[I] The results < median of time required to relieve pain > below were obtained according to the following conditions: a pain relief time is defined as when the pain index is "2 or lower," and when patients did not visit the hospital after the point 3, a pain index corresponding to a third date after the final hospital visit date (marked with '*') was assumed to be the point 2

[II] the first hospital visit date is represented by "Date 0", and the other dates after the first visit are represented by Date 1, Date 2 . . .

[III] pain level: patients were directed to record their pain levels by themselves in the scale of points 0 to 10

[IV] the date when patients do not visit the hospital is represented by '—'

[V] treatment begins within 72 hours after rash

Figure 3:
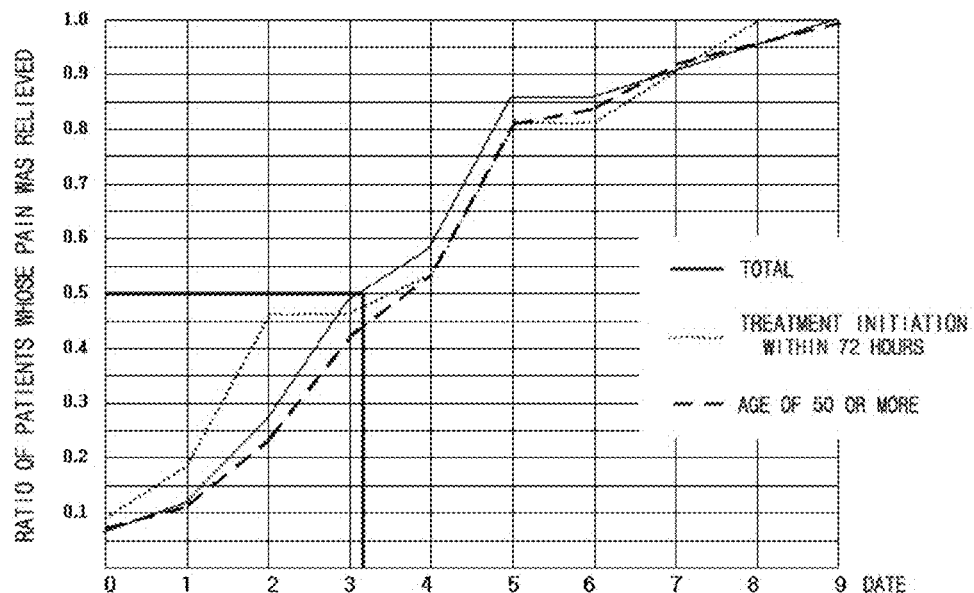
FIG. 3 shows a median of time required to relieve pain caused by herpes zoster.

Also, the median of time required to relieve pain is shown in FIG. 3.

5) Comparison with Meta-Analysis Data of Herpes Zoster Treatment

Comparison reference source: Can Fam Physician[Vol. 54, No. 3, March 2008, pp. 373-377]

<<Treatment of herpes zoster>> Wim Opstelten, MD PhD, Just Eekhof, MD PhD, Arie Knuistingh Neven, MD PhD and Theo Verheij, MD PhD Comparison results regarding a median of time required for generating scab over the whole skin lesion in a patient with herpes zoster are shown in Table 4 below.

TABLE 4

| Treatment Method | Median of time required for generating scab over the whole skin lesion (Day) |
|---|---|
| 500 mg of Famciclovir, three times per day, 7 days + application of H-Z cream | 2 |
| 500 mg of Famciclovir, three times per day, 7 days | 5 |
| Placebo | 7 |

Comparison results regarding a median of time required for relieving pain of a patient with herpes zoster are shown in Table 5 below.

TABLE 5

| Treatment Method | Median of time required for relieving pain (day) |
|---|---|
| 500 mg of Famciclovir, three times per day, 7 days + application of H-Z cream | 3.2 |
| 500 mg of Famciclovir, three times per day, 7 days | 20 |
| Placebo | 30 |

6) Progress into Post-herpetic Neuralgia

Typically, 20% of herpes zoster patients progress into post-herpetic neuralgia. However, among the total of 33 patients treated with the H-Z cream prepared according to Examples 1 to 3, no one progressed into post-herpetic neuralgia.

7. Post-herpetic Neuralgia Patient Analysis

1) Pain Lasting Time on Hospital Visit (Table 6)

TABLE 6

| | Pain lasting time on hospital visit (month) |
|---|---|
| Park Yeong-sook (48) | 1 |
| Choi Yeong-ja (68) | 3 |
| Chae Wan-jong (57) | 1 |
| Lee Yong-soon (53) | 1 |
| Kwon Hwa-sook (56) | 1 |
| Cha Aa-bu (65) | 1 |
| Lee Jeong-woo (63) | 2 |
| Choi Nak-won (48) | 1 |

2) Treatment Method

① H-Z cream (prepared according to Example 2) was applied (once per day on hospital visit)

② H-Z cream applying method: H-Z cream was applied on a skin lesion region in a thickness of about 3.0 mm and then sealed with polyethylene wrap 3) Pain Level Change Over Time[I] (in a Scale of 0 to 10) (Table 7)

TABLE 7

| | Date 0[II] | Date 1 | Date 2 | Date 3 | Date 4 | Date 5 | Date 6 | Date 7 | Date 8 | Date 9 |
|---|---|---|---|---|---|---|---|---|---|---|
| Park Yeong-sook (48) | 7[III] | 5 | 4 | [IV]— | — | 3 | — | — | * | — |
| Choi Yeong-ja (68) | 5 | 4 | 3 | — | 2 | — | — | — | — | — |
| Chae Wan-jong (57) | 8 | 6 | — | — | 4 | — | 3 | — | — | * |
| Lee Yong-soon (53) | 5 | 3 | 2 | — | 1 | — | — | — | — | — |
| Kwon Hwa-sook (56) | 8 | — | 5 | — | 3 | — | — | * | — | — |
| Cha Aa-bu (65) | 7 | 6 | 5 | 4 | 3 | 2 | — | — | — | — |
| Lee Jeong-woo (63) | 9 | — | — | 5 | — | — | 3 | — | — | * |
| Choi Nak-won (48) | 3 | — | 2 | — | — | — | — | — | — | — |

[I] The results < median of time required to relieve pain > below were obtained according to the following conditions: a pain relief time is defined as when the pain index is "2 or lower," and when patients did not visit the hospital after the point 3, a pain index corresponding to a third date after the final hospital visit date (marked with '*') was assumed to be the point 2

[II] the first hospital visit date is represented by "Date 0", and the other dates after the first visit are represented by Date 1, Date 2 . . .

[III] pain level: patients were directed to record their pain levels by themselves in the scale of points 0 to 10

[IV] the date when patients do not visit the hospital is represented by '—'

Figure 4:
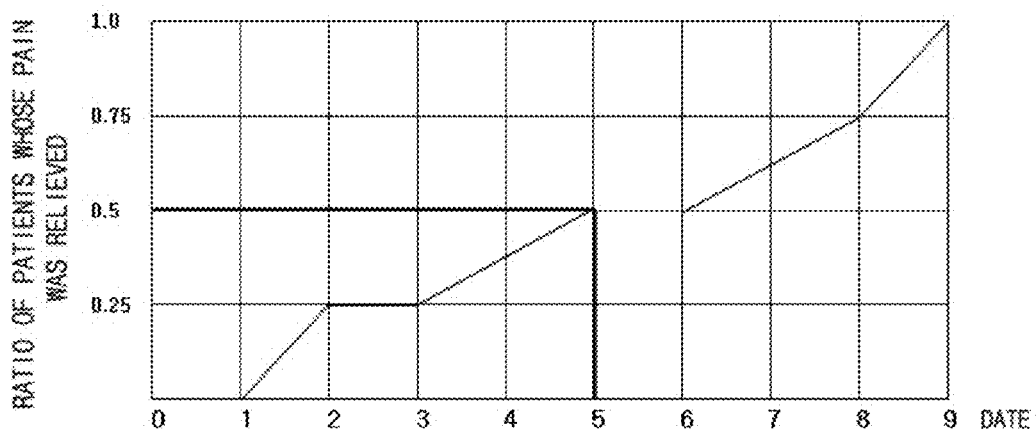
FIG. 4 shows a median of time required to relieve pain caused by post-herpetic neuralgia.

The median of time required to relieve pain is shown in FIG. 4.

4) Comparison with Meta-analysis Data of Post-herpetic Neuralgia Treatment

Comparison reference source: Can Fam Physicion [Vol. 54, No. 3, March 2008, pp. 373-377]

<<Treatment of herpes zoster>> Wim Opstelten, MD PhD, Just Eekhof, MD PhD, Arie Knuistingh Neven, MD PhD and Theo Verheij, MD PhD ① Comparison of median required for relieving pain in a patient with post-herpetic neuralgia (Table 8)

TABLE 8

| Treatment method | median required for relieving pain (date) |
|---|---|
| Applying of H-Z cream | 5 |
| Applying of 500 mg of Famciclovir, three times per day, for 7 days | 63 |
| Placebo | 119 |

8. Results and Analysis

1) Herpes Zoster Treatment Results and Analysis

① Among the total of 33 patients, only two were treated with only H-Z cream and the other patients (31 patients) were treated with Famciclovir (500 mg of one tablet for once, three times per day) and H-Z cream (applied once on hospital visit) simultaneously. The present clinical tests were performed to indirectly compare the effect of H-Z cream with meta-analysis data in patients to which Famciclovir was applied.

② Improvement effects on skin lesion in herpes zoster patients (median of time required to generate scab over the whole skin lesion) were compared with each other. The medians of 'placebo', 'Famciclovir alone,' and 'Famciclovir+H-Z cream' were '7 days', '5 days', and '2 days,' respectively (Tables 2 and 4, and FIG. 2). However, because the results were obtained from only the cases in which treatment begins within 72 hours after skin lesion was expressed in patients in meta analysis, it would be unreasonable to consider that the decrease (three days) in the skin lesion improvement date is significant (Table 4).

③ Improvement effects on acute pain in herpes zoster patients (median of time required to relieve pain) were compared with each other. The medians of 'placebo', 'Famciclovir alone,' and 'Famciclovir+H-Z cream' were '30 days', '20 days', and '3.2 days,' respectively (Tables 3 and 5, and FIG. 3). The results seem significant because the date differences are large even when, as described above, in metal analysis, the statistics subjects were restricted to only when treatment begins within 72 hours after skin lesion was expressed. Accordingly, it was confirmed that the H-Z cream is effective for improving acute pain of herpes zoster.

④ Typically, at an age of 50 or more, a herpes zoster development rate, skin lesion, pain, and a progress rate into post-herpetic neuralgia increase rapidly, and the administration of an antivirus agent within 72 hours after the expression of skin lesion affects a post-herpetic neuralgia treatment duration significantly. Accordingly, the pain relief effects were analyzed by dividing into a 50 or more-age group, a group that is subjected to treatment within 72 hours after expression of skin lesion, and the whole group (FIG. 3).

Compared to meta-analysis data, the use of H-Z cream lead to a substantial decrease in a pain relief level and a pain relief duration. However, when the H-Z cream was applied to the groups described above (the 50 or more-age group, the group that is subjected to antivirus treatment within 72 hours after expression of skin lesion, and the whole group), the groups showed similar acute pain relief levels and relief durations (FIG. 3 and Table 3). The results show that H-Z cream can be used to relieve a pain level and reduce a pain lasting duration, regardless of the age of patients and treatment initiation time (72 hours after expression of skin lesion).

⑤ The effect of H-Z cream on skin lesion was analyzed according to the 50 or more-age group, the group that is subjected to treatment within 72 hours after expression of skin lesion, and the whole group. However, there was no difference among the groups. Accordingly, it is considered that the administration of an antivirus agent, the age of a patient, and the treatment initiation time (72 hours after expression of skin lesion) do not significantly affect improvement on skin lesion.

⑥ Typically, a progress rate of herpes zoster into post-herpetic neuralgia is 20%. Accordingly, it is arithmetically reasonable to think that 6.6 patients, which is 20% of 33 herpes zoster patients, would develop post-herpetic neuralgia. However, in the present clinical tests using H-Z cream, no one developed post-herpetic neuralgia from herpes zoster and all of the patients were completely cured within 9 days after the treatment began. This result shows that H-Z cream is effective for repairing nerve tissues damaged by herpes zoster virus. Currently, a drug and method for reducing a progress rate into post-herpetic neuralgia together with an antivirus agent have not been developed. In this respect, the development of H-Z cream is meaningful.

⑦ It is reported that regarding herpes zoster treatment, an antivirus agent does not provide any advantageous effects on skin lesion improvement, pain reduction, treatment duration reduction, and progress rate into post-herpetic neuralgia. Only, in the case of 50 or more-age herpes zoster patients who are administered with an antivirus agent within 72 hours after expression of skin lesion, the post-herpetic neuralgia treatment duration is reduced (Famciclovir for the Treatment of Acute Herpes Zoster: Effects on Acute Disease and Postherpetic Neuralgia, A Randomized, Double-Blind, Placebo-Controlled Trial. Stephen Tyring, MD, PhD; Rick A. Barbarash, PharmD; James E. Nahlik, MD; Anthony Cunningham, MBBS, MD; John Marley, MD; Madalene Heng, MD; Terry Jones, MD; Ted Rea, MD; Ron Boon, BSc(Hons), CBio, MIBiol; Robin Saltzman, MD; the Collaborative Famciclovir Herpes Zoster Study Group. Annals of Internal Medicine, 1995, 123(2), pp. 89-96). That is, substantial treatment targets of herpes zoster patients are not antiviral activity but pain reduction and treatment duration reduction of acute pain, prevention of progress into post-herpetic neuralgia, and pain reduction and treatment duration reduction of post-herpetic neuralgia. In this aspect, it is considered that H-Z cream that has healing effects of pain reduction and treatment duration reduction of acute pain, prevention of progress into post-herpetic neuralgia, and pain reduction and treatment duration reduction of post-herpetic neuralgia through repair of damaged nerve tissues is useful.

2) Post-herpetic Neuralgia Treatment Results and Analysis

① The total of 8 patients in a clinical test were treated with H-Z cream alone.

② In meta analysis, subject patients who were treated with Famciclovir within 72 hours after expression of herpes zoster and progressed into post-herpetic neuralgia were clinically tested. However, in the present clinical tests, the herpes zoster treatment was not performed by the hospital described above from the beginning, and thus, corresponding treatment details were not able to be obtained.

③ Improvement effects on neuralgia in post-herpetic neuralgia patients (median for time required to relieve pain, FIG. 4) were compared to each other. The medians of 'placebo (Famciclovir was not administered in the herpes zoster treatment step)', 'Famciclovir (administered in the herpes zoster treatment step) alone', and 'H-Z cream' were '119 days', '63 days', and '5 days,' respectively (Table 8). The results also seem significant due to such large date differences, even when different comparison conditions between the present clinical test results and the meta-analysis data are taken into consideration. In particular, even when compared with a case in which an antivirus agent that is currently used in the herpes zoster step to reduce post-herpetic neuralgia treatment duration is administered (within 72 hours after expression of skin lesion), it is confirmed that the H-Z cream is more effective for reducing the post-herpetic neuralgia treatment duration.

3) Results

The most important thing in the clinical tests that were performed on herpes zoster and post-herpetic neuralgia patients is that herpes zoster did not progress into post-herpetic neuralgia. That is, nerve tissues that had been damaged in the herpes zoster step were recovered due to the application of H-Z cream. Accordingly, it is considered that the pharmaceutical composition is effectively applicable to other disease with neuronal damage, for example, acute inflammatory demyelinating peripheral polyneuropathy, chronic inflammatory demyelinating peripheral polyneuropathy, diabetic peripheral neuropathy, herpes zoster, vasculitis neuropathy, hereditary peripheral neuropathy, stroke, brain tumor, degenerative neurological disease, painful diabetic peripheral neuropathy, trigeminal neuralgia, carcinomatous neuro-pathy occurring along cerebral cortex or spinothalamic tract, post-traumatic neuropathy, post-herpetic neuralgia, phantom limb pain, post-stroke central pain and neuropathy of thalamic pain, or neuropathic pain.

Also, based on the assumption that the H-Z cream repairs neurons that are damaged in the herpes zoster step and thus, reduces pain levels in herpes zoster and post-herpetic neuralgia patients and prevents process into post-herpetic neuralgia from herpes zoster, whether H-Z cream or a major component of H-Z cream is effective for repairing damaged neurons was confirmed as follows.

EXPERIMENTAL EXAMPLE 2

Confirmation of Nerve Repair Effectiveness of H-Z Cream in Sciatic Nerve Crushing Injured Model To confirm the peripheral neuron repair effectiveness of the H-Z cream prepared according to Example 2, a sciatic nerve crushing injured model was treated by applying the H-Z cream thereto, and morphological evaluation and nerve conduction velocity evaluation were performed thereon.

In detail, 7-week 35 Sprague-Dawley male white rats were obtained and preliminarily raised for one week to make the rats to be accustomed to laboratory environments. This experiment started when the rats were 8-week old, and the preliminary raising and raising during the whole experimental duration were performed at a temperature of 23±2° C. and at a relative humidity of 60±10% in a room with 12 hours of a lightness and darkness cycle. Feed for lab animals and water were freely supplied. The lab animals were divided into three groups and each group included 10 rats. Crushing injury was induced in both sciatic nerves of the rats, and the rats were divided into a negative control with no treatment and a test group treated with H-Z cream.

1. Crushing Injury of Sciatic Nerve

The rats were administered with Ketamine hydrochloride (15 mg/100 g, Ketala®, Yuhan Co., Ltd) by intraperitoneal injection to induce general anesthesia, and then, hairs at both femoral regions were removed and a surgery site was disinfected with 10% Betadine solution and a surgery was carried out by using a conventional method under aseptic manipulation. A sciatic nerve was exposed and then, crushing injury was induced for 30 seconds by using a forceps having a tip diameter of 1 mm at 1 cm above a branch of tibial neuron and common peroneal neuron and then, muscle and skin were stitched up.

2. H-Z Cream Treatment

Regarding the test group, H-Z cream was applied to a skin where crushing injury was induced once per day for one, two, and three weeks.

3. Optical Microscope and Transmission Electron Microscope Test

Before and after the induction of crushing injury, and one, two, and three weeks after the H-Z cream treatment, general anesthesia was induced and damaged sciatic nerves were harvested by cutting. Regarding a normal control, both sciatic nerves were harvested by cutting by using the method described above without the induction of crushing injury. After a general tissue treatment process, a portion where the sciatic nerve fiber was cut perpendicularly to a progress direction at the point of crushing injury under observation with an optical microscope was selected.

Also, only the most representative neuron cross section was selected and observed by using an electron microscope.

Figure 5:
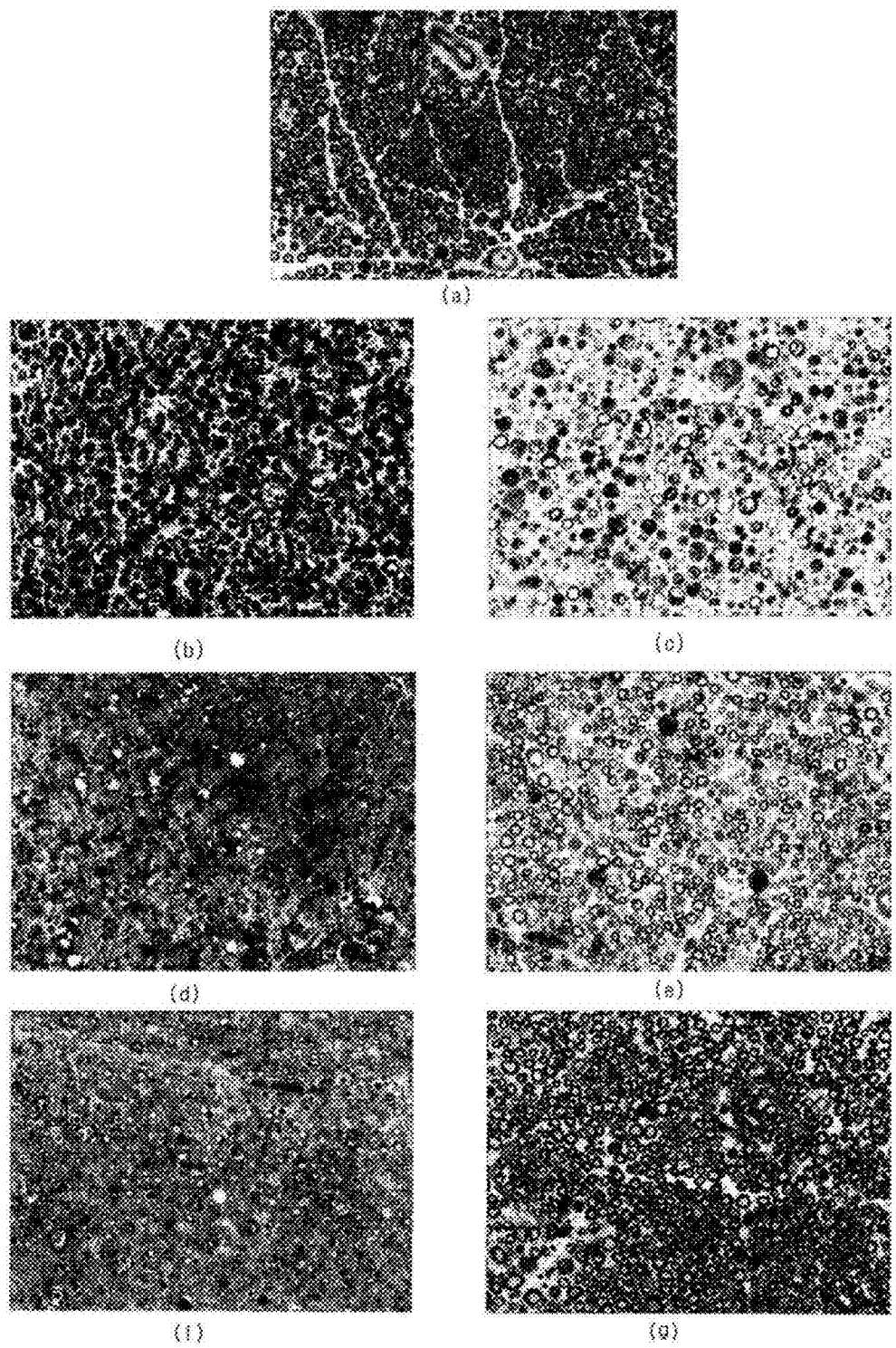
FIGS. 5 and 6 respectively show optical microscope and electron microscope images of nerve tissues that are treated with a phospholipid or sphingosine derivative contained in the pharmaceutical composition according to the present invention in a sciatic nerve crushing injured model (a: normal control, b: 1-week control, c: 1-week treatment, d: 2-week control, e: 2-week treatment, f: 3-week control, and g: 3-week treatment).
Figure 6:
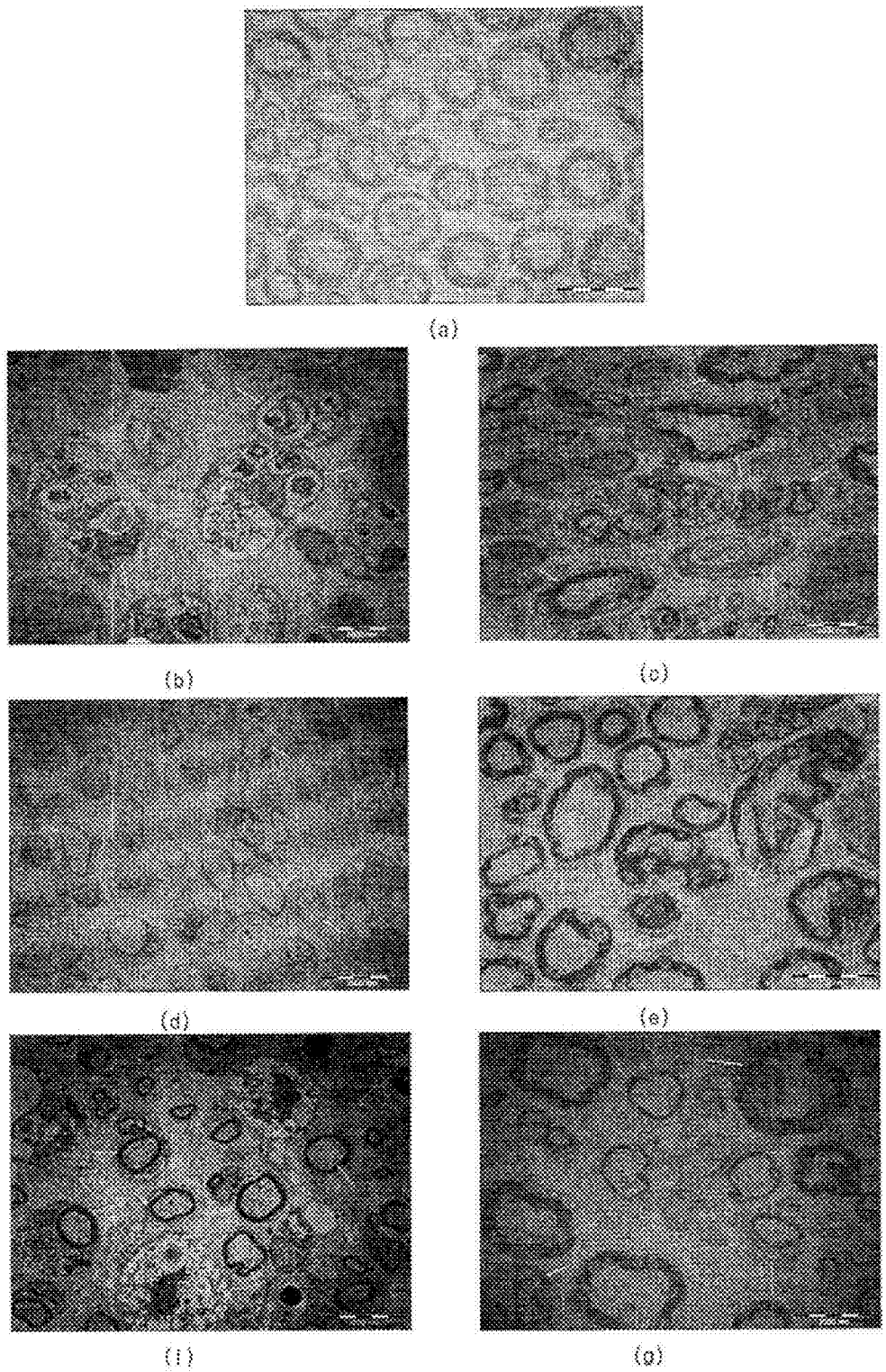

FIG. 5 shows optical microscopic images of a nerve tissue, and FIG. 6 shows electron microscopic images of a nerve tissue.

4. Electrophysiological Test

Before and after the induction of crushing injury and one, two, and three weeks after the H-Z cream treatment, a nerve conduction velocity test was performed by using an electromyogram evaluator (Multiliner, Tonnies Co., Ltd, Germany) while the temperature of the test room was maintained at a range of 23 to 27° C. The electromyogram evaluator was set as follows: a stimulus frequency of once per second, a stimulus time of 0.1 ms, a frequency width of 10 Hz to 10 KHz, a record sweep velocity of 5 ms/div, and a record sensitivity of 10 mV/div. Also, the stimulus was enhanced in phases until the amplitude of a compound muscle action potential was maximized. To perform a sciatic nerve test, white rats were fixed in a face-down position, a surface action electrode was located within muscle by attachment to a gastrocnemius central epidemis and a reference electrode was attached to a left leg. As a stimulus electrode, two under-skin coaxial needle electrodes were fixed to stimulate the exposed sciatic nerve directly. The a nerve conduction velocity test was performed at both sciatic nerves to measure nerve conduction velocity (m/s), and results thereof are shown in Table 9 below.

TABLE 9

| | | Immediately after crushing injury | After a predetermined duration | p-value |
|---|---|---|---|---|
| After one week | No treatment | 17.26 ± 7.34 | 18.76 ± 6.08 | 0.633 |
| | H-Z cream treatment group | 12.97 ± 4.07 | 23.67 ± 4.11 | 0.001 |
| After two weeks | No treatment | 13.26 ± 7.32 | 19.63 ± 6.05 | 0.051 |
| | H-Z cream treatment group | 14.37 ± 8.46 | 35.0 ± 3.53 | 0.001 |
| After three weeks | No treatment | 12.69 ± 7.36 | 34.54 ± 8.97 | 0.001 |
| | H-Z cream treatment group | 13.92 ± 6.73 | 47.01 ± 2.46 | 0.001 |

5. Evaluation of Damaged Myelinated Nerve Fiber Rate (Image Analysis)

A representative cross section portion was selected and a magnified image thereof (×400) was obtained by using a digital camera mounted on an optical microscope. From the image, the number of total myelinated nerve fibers and the number of denatured myelinated nerve fibers were counted by using an image analysis system.

That is, a neuron was accurately cut along a cross section thereof to prepare Epon block for optical microscope photographing and then Epon block was subjected to semi sectioning (thickness of 1 μm). The sectioning was stained with toluidine blue and a 400-time magnified microscopic image thereof was captured by using Olympus BX 51. From the obtained image, the number of total myelinated nerve fibers and the number of damaged myelinated nerve fibers were counted. Based on the results, a ratio of damaged myelinated nerve fibers per unit area was calculated and a mean thereof was evaluated by comparison. Results thereof are shown in Table 10 below.

TABLE 10

| Group | | Ratio of damaged myelinated nerve | p-value |
|---|---|---|---|
| Normal Control | | 0.04575 ± 0.0127 | |
| 1 week | Control | 0.9402 ± 0.0445 | 0.0019 |
| | Treatment | 0.6199 ± 0.1937 | |
| 2 weeks | Control | 0.2675 ± 0.2320 | 0.2886 |
| | Treatment | 0.2179 ± 0.0929 | |
| 3 weeks | Control | 0.1991 ± 0.0634 | 0.0895 |
| | Treatment | 0.1555 ± 0.0983 | |

EXPERIMENTAL EXAMPLE 3

Confirmation of Nerve Repair Effectiveness of H-Z Cream in Diabetic Neuropathy Model To confirm the peripheral neuron repair effectiveness of the H-Z cream prepared according to Example 2, a diabetic neuropathy white rat model was treated by applying the H-Z cream thereto, and morphological evaluation of tissue neuron and nerve conduction velocity evaluation were performed thereon.

In detail, 7-week 35 Sprague-Dawley male white rats were obtained and preliminarily raised for one week to make the rats to be accustomed to laboratory environments. This experiment started when the rats were 8-week old, and the preliminary raising and raising during the whole experimental duration were performed at a temperature of 23±2° C. and at a relative humidity of 60±10% in a room with 12 hours of a lightness and darkness cycle. Feed for lab animals and water were freely supplied. The lab animals were divided into a normal control (n=5), diabetes-induced control 1 (n=5), control 2 (n=5) that was not treated for 4 weeks after induction of diabetes, a test group 1 (n=5) that was treated with H-Z cream once per day immediately after induction of diabetes, and a test group 2 (n=10) that was treated with H-Z cream from 4 weeks after induction of diabetes.

1. Diabetes and Diabetic Peripheral Neuropathy Induction

The rats were treated once with 100 mg/kg of STZ (S-0130, streptozotocin, Sigma-Aldrich, USA) dissolved in a citric acid buffer (pH 4.5) by intraperitoneal injection. After 48 hours, blood was collected on empty stomach to measure blood sugar, and only white rats which had a blood sugar level of 240 mg/dL or more were used. In general, it is known that diabetic peripheral neuropathy occurs 4 weeks after induction of diabetes.

2. H-Z Cream Treatment

Regarding the test group, H-Z cream was applied to a skin region of both legs where sciatic nerves were distributed once per day.

3. Optical Microscope and Transmission Electron Microscope Test

General anesthesia was induced immediately after diabetic neuropathy was induced and at an appropriate time after H-Z cream treatment was performed, and then damaged sciatic nerves were harvested by cutting. Regarding a normal control, both sciatic nerves were harvested by cutting by using the method described above without the induction of diabetic neuropathy. After a general tissue treatment process, a portion where the sciatic nerve fiber was cut perpendicularly to a progress direction at the point of crushing injury under observation with an optical microscope was selected.

Also, only the most representative neuron cross section was selected and observed by using an electron microscope.

Figure 7:
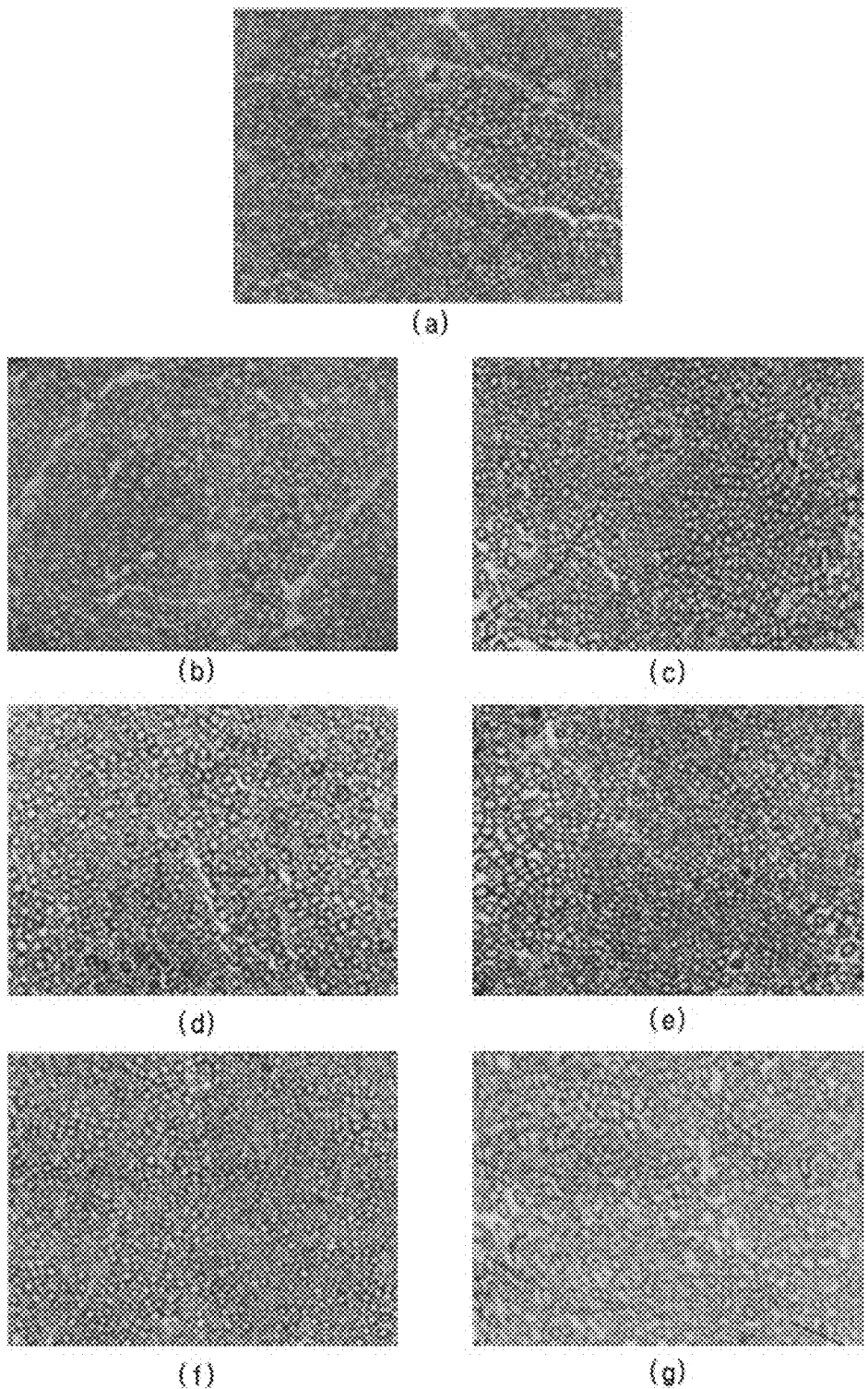
FIGS. 7 and 8 respectively show optical microscope and electron microscope images of nerve tissues that are treated with a phospholipid or sphingosine derivative contained in the pharmaceutical composition according to the present invention in a diabetic neuropathy model (a: normal control, b: 4-week no treatment after diabetes are induced, c: 4-week H-Z cream treatment after diabetes are induced, d: 5-week no treatment after diabetes are induced, e: 4-week no treatment after diabetes are induced, followed by 1-week H-Z cream treatment, f: 6-week no treatment after diabetes are induced, and g: 4-week no treatment after diabetes are induced, followed by 2-week H-Z cream treatment).
Figure 8:
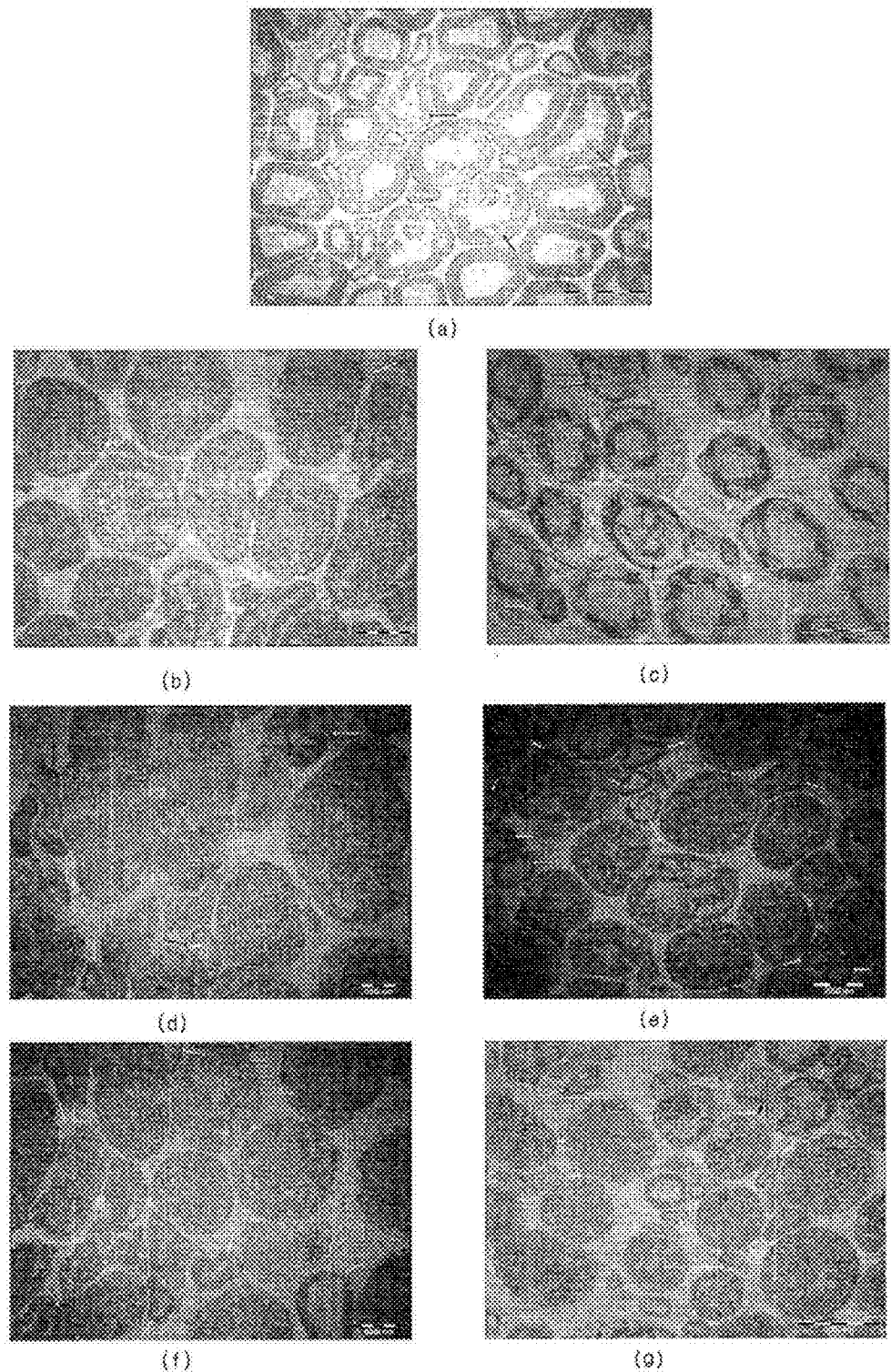

FIG. 7 shows optical microscopic images of a nerve tissue, and FIG. 8 shows electron microscopic images of a nerve tissue.

4. Electrophysiological Test

Before and after the induction of diabetic neuropathy, and at an appropriate time after the H-Z cream treatment, a nerve conduction velocity test was performed by using an electromyogram evaluator (Multiliner, Tonnies Co., Ltd, Germany) while the temperature of the test room was maintained at a range of 23 to 27° C. The electromyogram evaluator was set as follows: a stimulus frequency of once per second, a stimulus time of 0.1 ms, a frequency width of 10 Hz to 10 KHz, a record sweep velocity of 5 ms/div, and a record sensitivity of 10 mV/div. Also, the stimulus was enhanced in phases until the amplitude of a compound muscle action potential was maximized. To perform a sciatic nerve test, white rats were fixed in a face-down position, a surface action electrode was located within muscle by attachment to a gastrocnemius central epidemis and a reference electrode was attached to a left leg. As a stimulus electrode, two under-skin coaxial needle electrodes were fixed to directly stimulate the exposed sciatic nerve. The nerve conduction velocity test was performed at both sciatic nerves to measure nerve conduction velocity.

In this case, to confirm the neuron repair effectiveness of H-Z cream on diabetic peripheral neuropathy, Experiment 1 (H-Z cream treatment for 4 weeks after induction of diabetes; this experiment was performed to confirm a diabetic peripheral neuropathy prevention effect), Experiment 2 (no treatment for 4 weeks after induction of diabetes, followed by H-Z cream treatment for one week; this experiment was performed to confirm a diabetic peripheral neuropathy therapeutic effect) and Experiment 3 (no treatment for 4 weeks after induction of diabetes, followed by H-Z cream treatment for two weeks; this experiment was performed to confirm a diabetic peripheral neuropathy therapeutic effect) were conducted.

Nerve conduction velocity results when H-Z cream was applied for 4 weeks after induction of diabetes (Experiment 1) are shown in Table 11 below, and through variance analysis, the three groups all showed significant nerve conduction velocity.

TABLE 11

| Group | nerve conduction velocity (m/s) |
|---|---|
| Normal control | 62.0 ± 4.2 |
| Diabetes induction and no treatment | 32.4 ± 7.4* |

TABLE 11-continued

| Group | nerve conduction velocity (m/s) |
|---|---|
| Diabetes induction and 4 weeks of H-Z cream treatment | 50.6 ± 3.6* |

Also, nerve conduction velocity results when no treatment was performed for 4 weeks after induction of diabetes, followed by H-Z cream treatment for one week (Experiment 2) and when no treatment was performed for 4 weeks after induction of diabetes, followed by H-Z cream treatment for two weeks (Experiment 3) are shown in Table 12 below.

TABLE 12

| | At $4^{th}$ week after induction of DM | At $5^{th}$ week/$6^{th}$ week after induction of DM | p-value |
|---|---|---|---|
| No treatment for 5(4 + 1) weeks after induction of diabetes | 40.82 ± 3.15 | 36.25 ± 4.33 | .136 |
| No treatment for 4 weeks after induction of diabetes, followed by H-Z cream treatment for 1 week | 30.70 ± 6.68 | 45.00 ± 1.86 | .003 |
| No treatment for 6(4 + 2) weeks after induction of diabetes | 30.25 ± 4.41 | 31.08 ± 4.95 | .112 |
| No treatment for 4 weeks after induction of diabetes, followed by H-Z cream treatment for 2 weeks | 33.88 ± 6.69 | 45.55 ± 2.74 | .017 |

5. Evaluation of Damaged Myelinated Nerve Fiber Rate (Image Analysis)

A representative cross section portion was selected and a magnified image thereof (×400) was obtained by using a digital camera mounted on an optical microscope. From the image, the number of total myelinated nerve fibers and the number of denatured myelinated nerve fibers were counted by using an image analysis system.

That is, a neuron was accurately cut along a cross section thereof to prepare Epon block for optical microscope photographing and then Epon block was subjected to semi sectioning (thickness of 1 μm). The sectioning was stained with toluidine blue and a 400-time magnified microscopic image thereof was captured by using Olympus BX 51. From the obtained image, the number of total myelinated nerve fibers and the number of damaged myelinated nerve fibers were counted. Based on the results, a ratio of damaged myelinated nerve fibers per unit area was calculated and a mean thereof was evaluated by comparison. Results thereof are shown in Table 13 below.

TABLE 13

| Group | | Ratio of damaged myelinated nerve fibers (mean ± SD) | p-value |
|---|---|---|---|
| Normal control | | 0.04575 ± 0.0217 | |
| Diabetes-induced group | | 0.2994 ± 0.0946 | 0.2175 |
| Prevention Treatment group | | 0.2644 ± 0.0784 | |
| 1 week | Control | 0.5235 ± 0.0437 | 2.82562E−07 |
| | Treatment | 0.2248 ± 0.1611 | |
| 2 weeks | Control | 0.4063 ± 0.1428 | 0.0962 |
| | Treatment | 0.3093 ± 0.1559 | |

Diabetes-induced group: no treatment was performed for 4 weeks after induction of diabetes Prevention Treatment group: H-Z cream treatment was performed for 4 weeks after induction of diabetes 1 week: no treatment was performed for 4 weeks after induction of diabetes, followed by one-week of H-Z cream treatment 2 weeks: no treatment was performed for 4 weeks after induction of diabetes, followed by two-week of H-Z cream treatment

EXPERIMENTAL EXAMPLE 4

Confirmation of Nerve Repair Effectiveness of Lipobean® That Consists of Necessary Phospholipid Materials in Stroke Model (MCA-O Model)

To confirm a stroke therapeutic effect of necessary phospholipid materials contained in H-Z creams prepared according to Examples 1 to 3, Lipobean® was intravenously injected to MCA-O model white rats and then, a cerebral infarction level in the brain was observed to verify central neuron repair effectiveness.

That is, 7-week (body weight 230 to 250 g) male Sprague-Dawley white rats were obtained and the white rats were anesthetized for middle cerebral artery occlusion (MCAO) operation. Then, a nylon thread was inserted into a middle cerebral artery (MCA) of white rats to occlude the blood vessel for one hour, followed by reperfusion.

Lipobean® was injected to tail veins of white rats and the injection was initiated one hour before the MCAO operation. The injection was performed once per day for 14 days. The rats were divided into four test groups: a sham operation group (first experiment: 3 rats, and second experiment: 3 rats), a negative control group (vehicle control; first experiment: 3 rats, and second experiment: 2 rats), a Lipobean® 0.6 ml treatment group (first experiment: 3 rats, and second experiment: 3 rats), and a Lipobean® 1.2 ml treatment group (first experiment: 3 rats, and second experiment: 3 rats).

1. General Behavior Test

Before and after daily treatment, a general behavior was observed with the naked eyes, and the results are compared with control. Compared to the control group, the treatment region of the tail of the negative control and the drug treatment group showed necrosis. However, the results did not affect the overall experiment significantly. In the case of the rats which experienced a large weight loss, a serious sedation occurs. However, the general behavior of the other rats is barely changed.

2. Body weight

Figure 9:
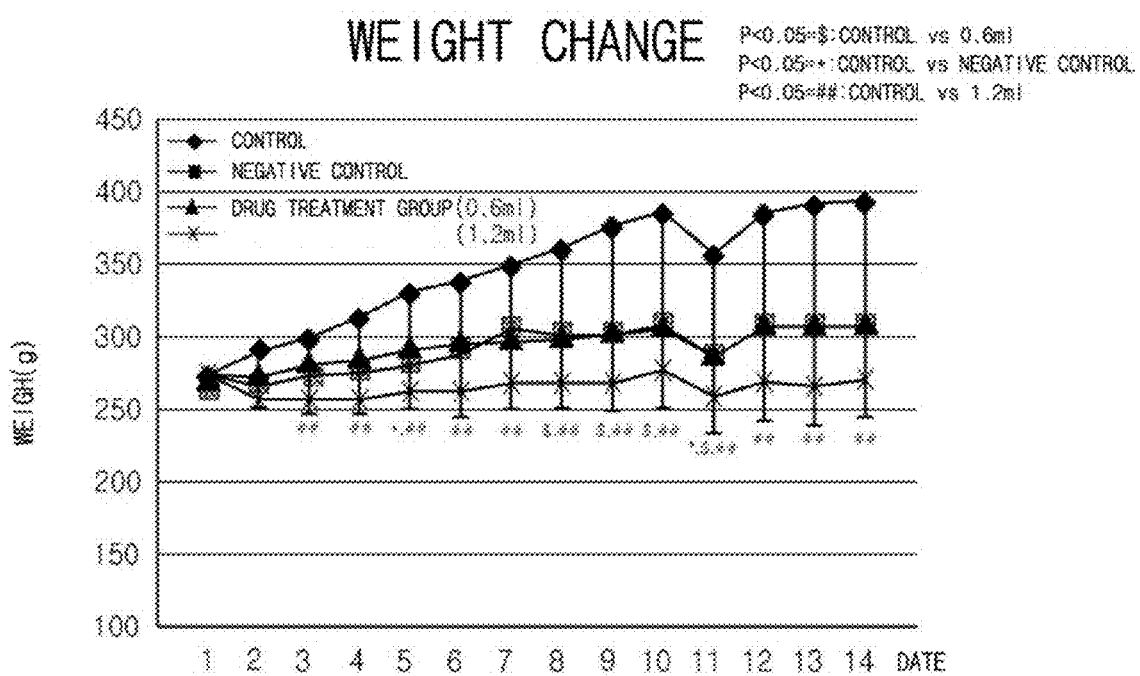
FIG. 9 shows a body weight change in a stroke model according to treatment with a phospholipid or sphingosine derivative contained in the pharmaceutical composition according to the present invention.

Weight change was measured everyday once per day at 4 p.m., and as shown in FIG. 9, the negative control shows a statistically significant difference at $5^{th}$ date and $11^{th}$ date compared to the control, and the low dosage drug treatment group (0.6 ml) shows a statistically significant difference at $8^{th}$ date, $9^{th}$ date, $10^{th}$ date, and $11^{th}$ date compared to the control. The high dosage drug treatment group (1.2 ml) shows a statistically significant difference for all the whole treatment duration except for $1^{st}$ date and $2^{nd}$ date (One-Way ANOVA, Tukey's Multiple Comparison Test).

3. Cerebral Infarct Area Interpretation

Fourteen days after Lipobean® treatment, the brain was extracted and stained with 2,3,5-triphenylterazolium chloride (TTC) and cerebral infarct areas of the respective test groups were compared. In detail, the extracted brain was perpendicularly cut from a frontal pole by an interval of 2 mm by using Brain Matrix and the sectionings were immersed in a 2% TTC solution of which temperature was maintained at a temperature of 37° C. while light was shielded. About one to two minutes later, only a damaged tissue portion (cerebral infarction portion) remained white and a normal tissue was stained with red. This was placed in a 4% paraformaldehyde solution and fixed, and on the following date, the tissues were photographed by using a digital camera. From the pictures, the cerebral infarct area was measured by using an image-pro plus program and the results were analyzed using a Graphpad Prism 4.0 program.

Figure 10:
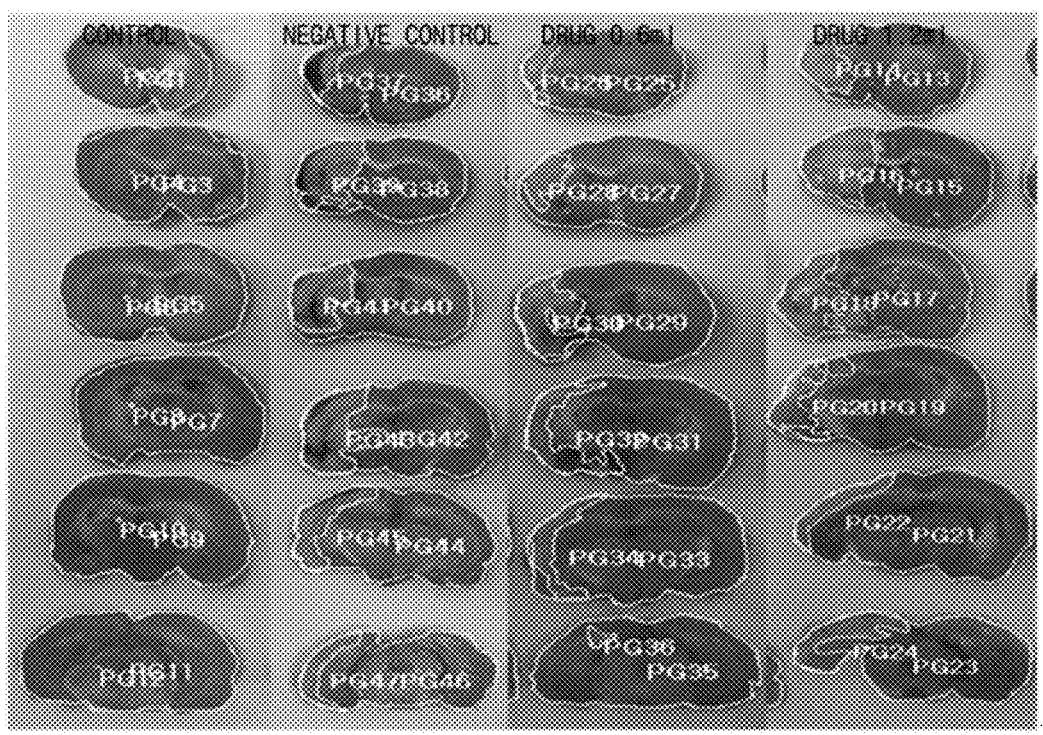
FIGS. 10 and 11 respectively show TTC staining pictures of a brain tissue of a stroke model according to treatment with a phospholipid or sphingosine derivative contained in the pharmaceutical composition according to the present invention, and a cerebral infarct area.
Figure 11:
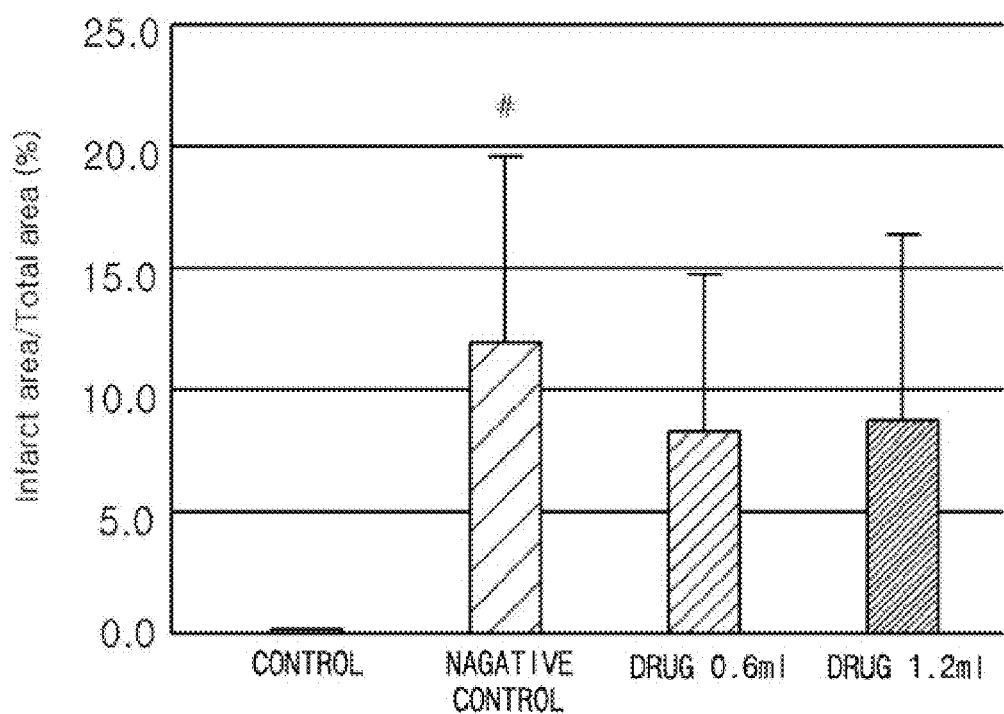

The cerebral infarct area was evaluated as a percent (%) of the area of a cerebral infarction portion based on the whole area of the respective brain tissues. As shown in FIGS. 10 and 11, the low dosage drug treatment group (0.6 ml) and the high dosage drug treatment group (1.2 ml) showed slightly significant treatment effects. (One-Way ANOVA, Tukey's Multiple Comparison Test.).

What is claimed is:

1. A method of treating neuropathic pain, comprising:
administering a pharmaceutical composition to a skin surface of a subject experiencing the neuropathic pain, the pharmaceutical composition comprising a lecithin as an active ingredient, aloe vera gel, alpha-tocopherol, and propyl benzoate,
wherein the pharmaceutical composition is formulated for a topical administration to the subject,
wherein the neuropathic pain comprises herpes zoster, post-herpetic neuralgia, and diabetic neuropathic pain.

2. The method of claim 1, wherein the pharmaceutical composition further comprises vegetable gel, a vegetable resin, and a synthetic resin.

3. The method of claim 2, wherein the vegetable gel, vegetable resin, and synthetic resin is selected from the group consisting of aloe gel; a seaweed extract selected from the group consisting of kelp extract, agar extract, and Fucoidan; and a mixture thereof.

4. The method of treating pain claim 1,
wherein the lecithin is included ranging from 1.7 wt % to 3.24 wt % of the pharmaceutical composition.

5. The method of claim 4, wherein said formulation of the pharmaceutical composition is selected from the group consisting of an ointment, a lotion, a cream, and a topical-transdermal patch.

* * * * *